US008628553B2

(12) United States Patent
Voegele et al.

(10) Patent No.: US 8,628,553 B2
(45) Date of Patent: Jan. 14, 2014

(54) EXPANDING ADHESIVE FOAM STRUCTURE TO REDUCE STOMACH VOLUME

(75) Inventors: James W. Voegele, Cincinnati, OH (US); Douglas J. Turner, Cincinnati, OH (US); Mark S. Ortiz, Milford, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1399 days.

(21) Appl. No.: 11/557,649

(22) Filed: Nov. 8, 2006

(65) Prior Publication Data
US 2008/0109086 A1 May 8, 2008

(51) Int. Cl.
*A61M 29/00* (2006.01)
(52) U.S. Cl.
USPC .......................................................... 606/191
(58) Field of Classification Search
USPC ................ 606/191, 151, 192, 195; 623/23.65
See application file for complete search history.

(56) References Cited

U.S. PATENT DOCUMENTS

| 5,990,378 | A  | * | 11/1999 | Ellis .......................... 623/11.11 |
| 6,458,095 | B1 | * | 10/2002 | Wirt et al. ....................... 604/82 |
| 6,802,822 | B1 | * | 10/2004 | Dodge ............................. 604/82 |
| 6,852,330 | B2 | * | 2/2005  | Bowman et al. ............. 424/426 |
| 7,037,344 | B2 |   | 5/2006  | Kagan et al. |
| 7,144,878 | B2 |   | 12/2006 | Mihalik |
| 2004/0024386 | A1 | * | 2/2004  | Deem et al. ....................... 606/1 |
| 2004/0117031 | A1 | * | 6/2004  | Stack et al. ................ 623/23.65 |
| 2005/0192599 | A1 | * | 9/2005  | Demarais ....................... 606/151 |
| 2006/0281970 | A1 | * | 12/2006 | Stokes et al. ................... 600/104 |
| 2007/0100369 | A1 | * | 5/2007  | Cragg et al. ................... 606/192 |

FOREIGN PATENT DOCUMENTS

WO    WO 92/09651    6/1992

* cited by examiner

*Primary Examiner* — Katherine Dowe
*Assistant Examiner* — Jonathan Hollm

(57) ABSTRACT

Expanding or foaming adhesives are used to reduce the stomach volume to reduce the caloric intake and weight of a patient. A web structure is attached inside the stomach and an expanding or foaming adhesive is applied to the web structure. The expanding or foaming adhesive attaches to the web structure and to the stomach to partition the stomach. The partition barrier divides the stomach volume into a reduced volume available for food storage and an empty volume that the food cannot enter. The reduced volume enables the patient to feel full faster and reduce caloric intake. A passageway can be provided between the two volumes near the base of the stomach to allow food or fluids to exit from the empty volume.

17 Claims, 6 Drawing Sheets

EXPANDING ADHESIVE FOAM STRUCTURE TO REDUCE STOMACH VOLUME

FIELD OF THE INVENTION

The present invention relates, in general, to medical instruments used for bariatrics and, more particularly, to instruments and methods for reducing the size of a stomach by placing an implantable barrier structure within the stomach.

BACKGROUND OF THE INVENTION

Food passes from the esophagus to the stomach. After entering the stomach, the food is stored in order to allow the stomach to chemically and mechanically prepare the food for receipt in the small intestine where the food is further digested. Food does not enter the bloodstream through the walls of the stomach. Thus, the stomach has complete control over the passage of food to the small intestine to ensure the food is ready both chemically and physically.

Statistics estimate that approximately sixty-four percent of Americans are overweight including the thirty percent of Americans whom are obese. As medical problems mount relating to overweight lifestyles, more Americans opt to undergo medical operations as a means for decreasing their appetite. A common theme among the operations is to reduce the volume size of the stomach. Reducing the volume size of the stomach physically prevents an individual from eating an excessive amount of food.

A wide range of methods exist for decreasing the volume size of a stomach. These methods range from stapling the stomach to inserting a volumetric object inside the stomach to reduce the stomach volume available for food retention. Both options limit the amount of food entry possible as compared to the period before the procedure is performed. Certain advantages and drawbacks of each method relate to the invasiveness of the procedure, success rate, maintenance, cost, length, and removability.

Stapling a patient's stomach or resecting the stomach with a stapler are both ways to create a smaller stomach volume. Attaching a volumetric object or reducer within a patient's stomach is another. An inflatable balloon placed in the stomach is taught in U.S. Pat. No. 6,981,978 by J. Gannoe as a way to decrease the stomach volume. The inflatable balloon can be inserted trans-orally in a deflated condition and inflated within the patient.

Suturing the stomach walls together and creating stomach partitions are also techniques used to reducing the caloric intake of a patient. U.S. Pat. No. 7,037,344 by Kagan et al. teaches bringing the walls of the stomach together with suture or staples to create a partition or pouch for the treatment of morbid obesity.

Creating a stomach partition by bringing stomach walls together and inflating a volumetric object are both known in the art. Building an implantable partition within the stomach from an expanding foam is not well known to those skilled in the art. Attaching a balloon or a foam structure to a stomach wall within a harsh stomach environment can also present challenges. U.S. Patent Application 2002/0147462 discloses foaming adhesives and is hereby incorporated by reference in its entirety. International publication WO 92/09651 by Cooke et al entitled "Polycyanoacrylate Foam" also describes expanding foams.

At present, there are no known surgical implants, instruments to apply the implants, or methods of placing the implant that can meet all of the needs outlined above. These and other advantages will become more apparent from the following detailed description and drawings.

SUMMARY OF THE INVENTION

The present invention An implant device for partitioning a stomach to achieve weight loss is disclosed. The implant device has a web structure that comprises one or more filaments that are attachable to the stomach wall. A foam partition is provided about the web structure. The foam partition partitioning the stomach into a food digestion portion and at least one empty portion. The partition reduces the size of the stomach available for food storage and digestion.

Alternately, a surgical device for reducing the weight of a patient by partitioning a stomach is disclosed. The surgical device has a web structure attached about the inner wall of the stomach, an expandable adhesive foam, and an adhesive foam system to apply the expandable adhesive foam. The expandable adhesive foam is applied to one or more of the attached web structure and the inner wall of the stomach. The expandable adhesive foam and the web structure partitions the stomach into a digestion portion and an empty portion.

These and other objects and advantages of the present invention shall be made apparent from the accompanying drawings and the description thereof.

BRIEF DESCRIPTION OF THE FIGURES

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Bariatrics plays a major role in obesity. Generally, obesity is a condition that when left unaddressed leads to numerous health problems. Surgical intervention to reduce stomach volume to avoid health problems is common today. FIGS. 1 through 6 illustrate a trans-oral method for reducing stomach volume by placing a foam partition in the stomach that may be performed quicker and with less intrusion into the body. Quicker surgery and reduced invasiveness lead to a lower surgery cost, a shorter recovery time, and reduced pain.

The Device

Figure 1:
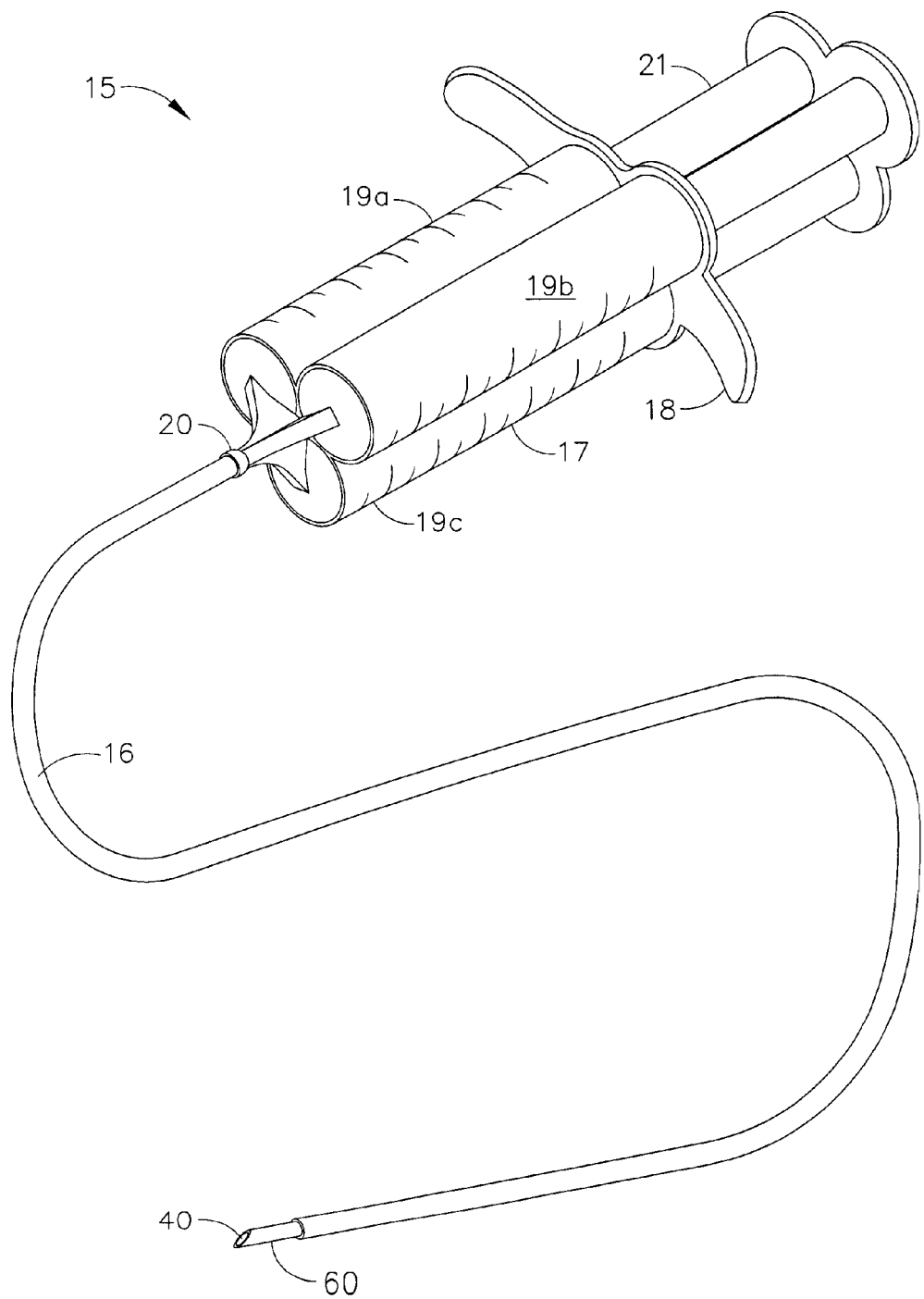
FIG. 1 is a perspective view of a surgical device for the creation of an expanding foam used as a surgical implant.

Turning to the Drawings, wherein like numerals denote like components throughout the several views, FIG. 1, shows a foam-producing surgical device 15 capable of partitioning a patient's stomach with an expanding adhesive foam structure or wall 29. The wall 29 divides the patient's stomach into a food digestion portion and an empty portion and reduces the stomach volume available for food. This volume reduction enables a patient to eat a small amount, fill up the smaller available digestive portion of the stomach, and feel full. Surgical device 15 dispenses an expandable foam 28 (FIG. 5) through a cannula or hose 16 inserted into a patient's stomach.

The expandable foam 28 is a combination of foam components. For the example shown, the expandable foam 28 is a mix of foam components comprising an adhesive (not shown), a foaming agent (not shown), and an adhesive initiator (not shown). Combining the adhesive and foaming agent produces an expanding adhesive foam. Adding the adhesive initiator (not shown) to the adhesive (not shown) and foaming agent (not shown) sets or polymerizes the expanding foam 28 containing into a solid structure.

The foam-producing device 15 has a housing 17 to contain the foam components therein. The housing comprises a handle 18 for the surgeon to hold, a first chamber 19a, a second chamber 19b and a third chamber 19c to hold the foam components therein and at least one plunger or pump 21 to dispense the foam components from the foam producing device in a mixed or neat state. A mixer 20 is provided downstream of the pump 21 to mix the foam components into expanding foam 28. Pump 21 dispenses the foam components as pressure is applied to advance the pump 21 towards the handle 18 and through the chambers 19a, 19b, and 19c. The foam components are mixed together in mixer 20 after exiting chambers 19a, 19b, and 19c. After mixing, the foam 28 travels through the hose 16 and exits from a nozzle 60 having one or more foam dispersement ports 40 at a distal end of the hose 16. To create an implantable wall 29 or surgical implant in the stomach, a suture web 27 is first created from suture 30 and attached about the inner stomach wall with a piercing device. Second, the expanding foam 28 is dispensed from the surgical device 15 to adhere to the suture web 27 and the stomach wall, and create the surgical implant device to partition the stomach.

The Method

Figure 2:
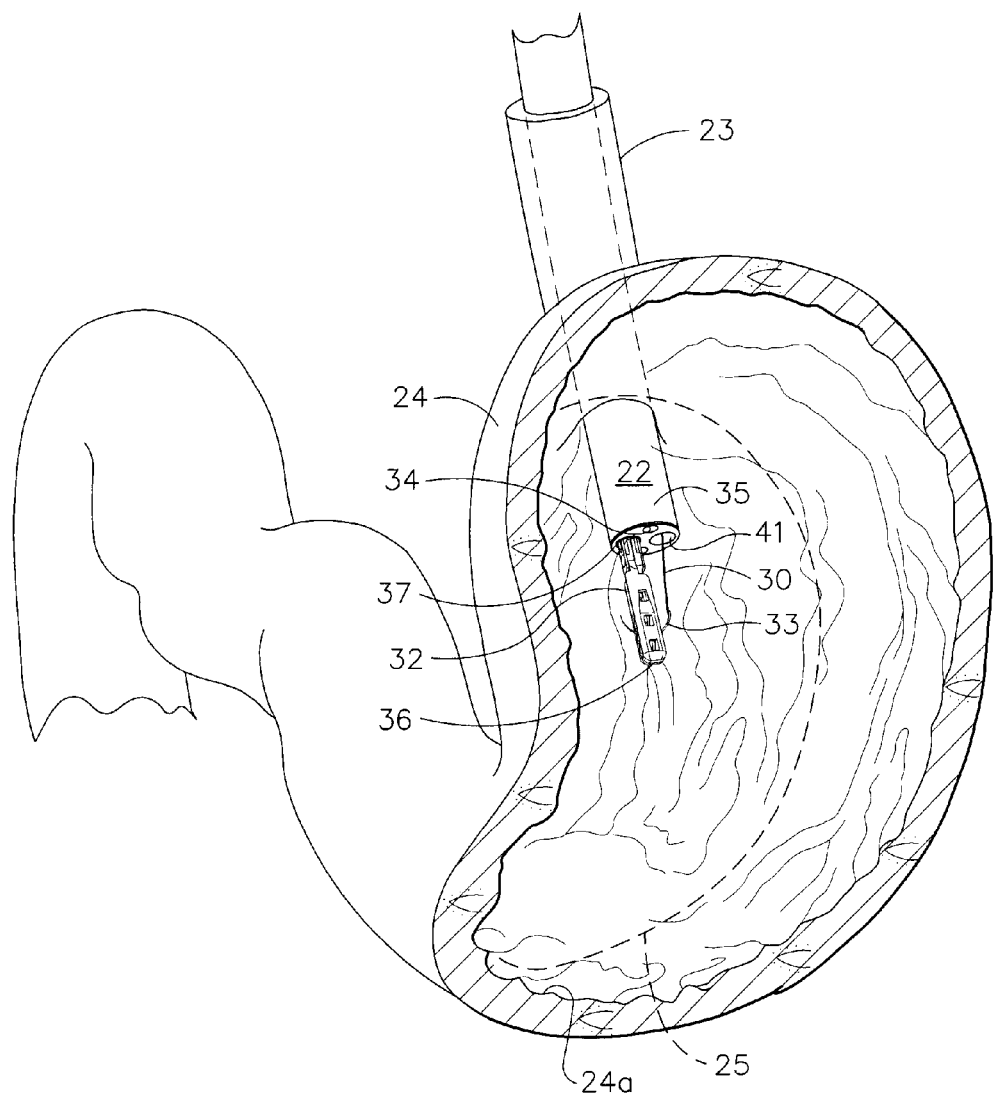
FIG. 2 is a front cross-sectional view of the stomach with an endoscope penetrating the stomach and a dashed line representing the planned location for a plurality of stitches.

FIG. 2 illustrates a front, cross-sectional view of a stomach 24. An endoscope 22 travels trans-orally through an esophagus 23 into the stomach 24. The endoscope 22 is positioned in such a manner whereby the surgeon is viewing the inside of the stomach 24 and planning to sew suture 30 along a dashed line 25. The dashed line 25 represents a desired location of suture attachment points. The endoscope 22 has a plurality of access passageways extending through to a distal end 35 permitting the surgeon to insert numerous tools through the endoscope 22. The passageways are capable of permitting the advancement of such tools as cameras, needles, suture, and foam through the apertures. The distal end 35 of the endoscope 22, as seen in FIG. 2, has two passageway apertures 37 and 41 and a camera 34. A grasper 32 is shown extending from aperture 37 and holds a needle 33 with suture 30 within jaws 36 of grasper 32. The suture 30 is of sufficient strength to be capable of withstanding the harsh environment of the stomach 24. In the medical device world, suture 30 can be a separate strand, or suture 30 can be attached to needle 33. In either case, the strand and/or combination of strand and needle are generally referred to as suture.

Figure 3:
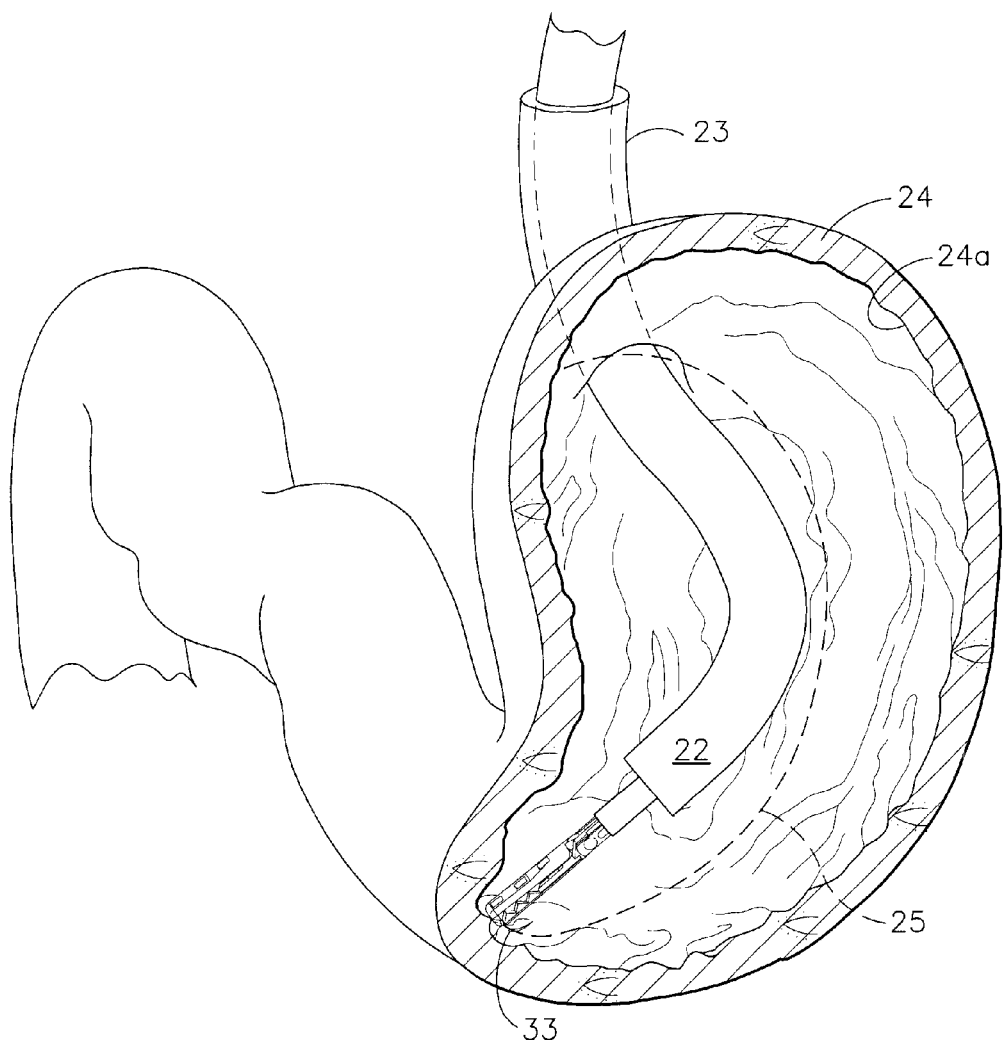
FIG. 3 is a front cross-sectional view of the stomach with an endoscope penetrating the stomach and beginning to stitch a suture web across the stomach along the dashed line.

FIG. 3 represents a front, cross-sectional view of the stomach 24 where the surgeon advances the endoscope 22 adjacent to the dashed line 25 representing the desired location of suture attachment points. As seen in FIG. 3, after advancing the endoscope 22 adjacent to the dashed line 25, the surgeon begins weaving a loose suture web 27 (FIG. 4) inside the stomach 24 along dashed line 25. The surgeon is using a penetration device or needle 33 to attach the suture web 27 to a stomach wall 24a by placing needle 33 through tissue at a first point on line 25.

Figure 4:
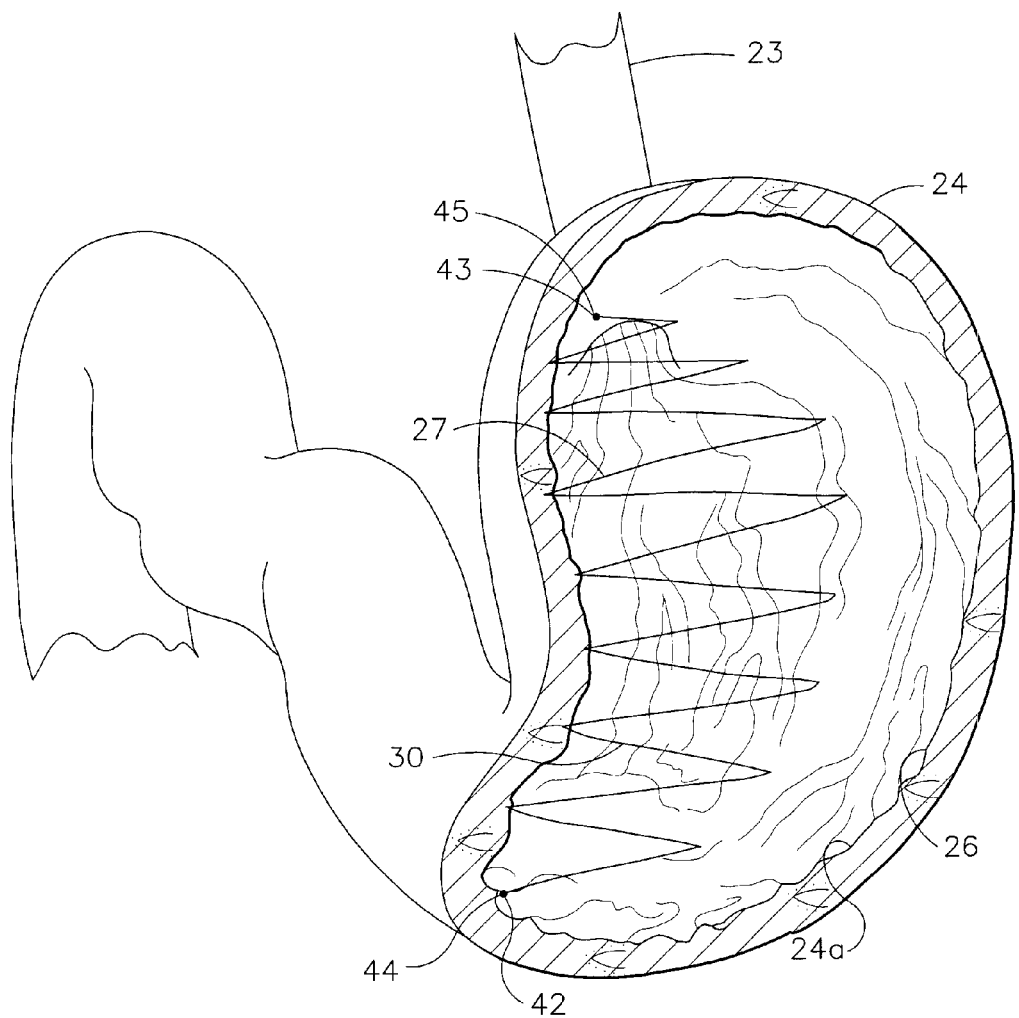
FIG. 4 is a front cross-sectional view of the stomach illustrating the completed suture web structure across the stomach.

In FIG. 4, the suture web 27 is shown placed from side to side across the stomach 24 with no tension on the suture. Without tension, the suture web 27 does not approximate or bring together the stomach inner walls 24a, and this reduces tissue stress loads at the suture locations. If the suture web 27 has tension, the tissue can tear, releasing the suture web. The suture web 27 described above is not limited solely to hand sutured suture webs 27 constructed from suture 30. For example, the suture web 27 can be a pre-shaped or woven mesh or web structure that is inserted into the patient and attached to the stomach wall (not shown). The suture web 27 could be shaped or created in any manner deemed necessary by the surgeon whereby the suture web 27, when combined with an expanding foam 28, produces a wall 29 capable of partitioning the stomach 24. The suture web 27 is shown attached to the stomach wall by suturing with a needle; however the attachment of suture web 27 is not solely limited to this type of attachment. For example, a pre-woven suture web could be attached to the stomach by a tissue piercing device or fastener such as a staple, a clip, a corkscrew fastener, a barb, a clamp, or any other fastener that can attach a suture web to tissue.

Suture web 27 can be absorbable or non-absorbable, depending on surgeon's preference. Suitable materials for an absorbable suture 27 can include, but is not limited to catgut, polyglycolic acid, polyglactin, polydioxanone, nylon and polyglyconate. Suitable non-absorbable suture materials can include, nylon, Dacron, polypropylene, braided polyester, and polybutester.

In FIG. 4, the surgeon has completed a suture web 27 and retracted any instruments into the endoscope 22. The completed suture web 27 crisscrosses the patient's stomach along the dashed line 25 of FIG. 2. A lower attachment point 42 and an upper attachment point 43 illustrate a general scheme for weaving the suture web 27. The general scheme involves varying the location of adjacent attachment points in a manner where the attachment points alternate being located on opposite locations within the stomach 24. This alternating scheme generally produces the suture web 27. The suture web 27 is tied at opposing ends to help ensure stability. Thus, a first tying point 44 is located on the suture web 27 at the first stitch of suture. Additionally, a second tying line 45 is located on the suture web 27 where the surgeon makes the last stitch. The location of the tie attachments may vary depending upon a variety of factors including but not limited to the size of stomach, size of partition, type of suture and surgeon's desires. After completing the suture web 27, any remaining suture is removed from the stomach 24. Whereas a suture web sewn into tissue is disclosed, other examples of web structures and fastening devices can include, but are not limited to a mesh or web structure attached to the stomach walls by any one of a number of fasteners such as staples.

Figure 5:
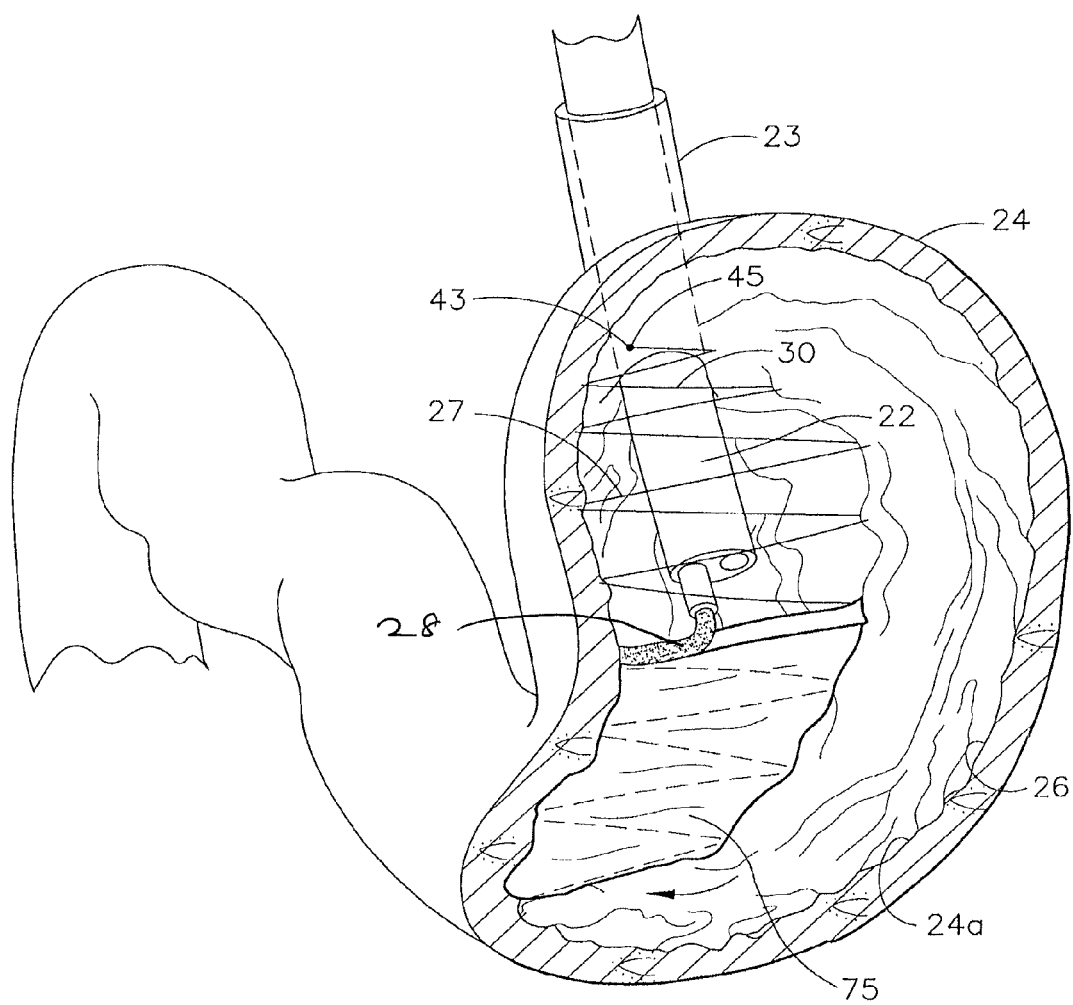
FIG. 5 is a front cross-section view of the stomach illustrating the surgical device applying the expandable foam across the suture web and the stomach to create a surgical implant that partitions the stomach.

FIG. 5 represents a front, cross-sectional view of the stomach 24 where the surgeon has begun dispensing an expandable foam 28 to partition the stomach 24. As shown in FIG. 5, after constructing the suture web 27, the grasper 32, the needle 33 and any remaining suture 30 are removed from the stomach 24 by being retracted out of the endoscope 22. Hose 16 is now advanced through the endoscope 22 until nozzle 60 and foam dispersement port 40 of the hose 16 exits aperture 37 of the endoscope 22. Pressure from the plunger 21 forces the foam components of expandable foam 28 to travel from chambers 19a, 19b and 19c. As the expandable foam 28 exits chambers 19 and 20, the expandable foam 28 is mixed together. The expandable foam 28 then enters the hose 16. The foam 28 then travels through the hose 16 and into the stomach 24. After the foam travels the length of hose 16, the foam 28 exits the distal end 40 of hose 16. As stated earlier, the distal end 40 of hose 16 hangs adjacent to the aperture 37. After exiting the distal end 40, the expandable foam 28 is dispensed within the suture web 27 to produce a partition or wall 29 within the stomach 24. The wall 29 partitions the stomach 24 into two distinct, smaller volumes. Food entering the stomach 24 may only pass through the stomach volume contained between the esophagus 23 and a pyloric sphincter 39. The precise location of each wall 29 will vary according to multiple factors including but not limited to the surgeon's preference, the stomach size and the volume reduction required.

As stated earlier, the foam 28 is capable of expanding. The adhesive (not shown) used in the foam can be a polymerizable adhesive such as a polymerizable monomer or a cyanoacrylate. Suitable materials for adhesive (not shown) may be, for example, monomers and monomer systems, acrylate, epoxy, urethane, silicone, silicone rubber, photopolymerizable compositions, vinyl-terminated monomers, gelatin resorcinol formaldehyde, gelatin resorcinol glutaraldehyde, anhydrides cross-linked with polyols, hyaluronic acid cross-linked with hydrazines, mixed monomer systems and co-polymers. Particularly suitable polymerizable materials, such as polymerizable monomers, and the polymerization products thereof expand under certain conditions, such as with heat, or with an added agent, such as a foaming agent (not shown).

Foaming agent 51 can be combined with the polymer material 50 to create the foam 28 or foaming agent 51 could be a catalyst that reacts with a compound in adhesive 50. For example, an adhesive 50 such as various monomers, particularly cyanoacrylate monomers, may be mixed with organic liquids or foaming agents 51, and polymerization initiators 52 (see below), to form a composition that polymerizes and expands into, for example, a polycyanoacrylate foam. Suitable foaming agents 51 include pentane, hexane, heptane, 1,1,2-trichlorotrifluoro-ethane, 1,1,1-trichlorotrifluoroethane-, petroleum ether, diethyl ether, cyclopentane, cyclohexane, benzene, carbon tetrachloride, chloroform, methylcyclopentane, dimethylsulfide, 1,1-dichloroethane, 1,1,1-trichloroethane, perfluorohexane, perfluoroheptane, 1-bromopropane and any combination thereof. Examples of suitable compositions that form expanding foams 28 are disclosed in U.S. patent application 2002/0147462 entitled "Bronchial Occlusion Method and Apparatus", the entire disclosure of which is hereby incorporated in its entirety by reference. Additionally, pump 21 is not limited to the plunger embodiment described above. By way of example, one or more foaming agents 51 can be used as an aerosol or pump to draw, siphon, and/or propel components of adhesive 28 from the nozzle 60.

An adhesion initiator (not shown) can be used to polymerize the foam 28 into a solid expanded foam structure. For this example, a polymer cyanoacrylate adhesive is chosen as the base polymer material of the foam. Polymerization of the foam 28 can be initiated by stomach moisture or by contact of the adhesive with an adhesion initiator (not shown). Adhesion initiator (not shown) can be mixed with the foaming agent (not shown), be a second part of a two part adhesive (not shown), or placed upon the suture 27 before or during the surgery. Contact with the adhesion initiator polymerizes the expandable foam 27. Suitable adhesion initiators (not shown) can include, but are not limited to, detergent compositions; surfactants: e.g., nonionic surfactants such as polysorbate 20 (e.g., Tween 20.TM. from ICI Americas), polysorbate 80 (e.g., Tween 80.+-.from ICI Americas) and poloxamers, cationic surfactants such as tetrabutylammonium bromide, butyrylcholine chloride, anionic surfactants such as sodium tetradecyl sulfate, and amphoteric or zwitterionic surfactants such as dodecyldimethyl(3-sulfopropyl)ammonium hydroxide, inner salt; amines, imines and amides, such as imidazole, tryptamine, urea, arginine and povidine; phosphines, phosphites and phosphonium salts, such as triphenylphosphine and triethyl phosphite; alcohols such as ethylene glycol, methyl gallate, ascorbic acid, tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat 336; organometallics such as cobalt naphthenate and manganese acetylacetonate; and radical initiators and radicals, such as di-t-butyl peroxide and azobisisobutyronitrile. The polymerizable and/or cross-linkable material may also contain an initiator that is inactive until activated by a catalyst or accelerator. Examples of suitable polymer materials, foaming agents and polymerization initiators are taught in U.S. Patent Application 2004/0147462 which is hereby incorporated by reference in its entirety.

Figure 6:
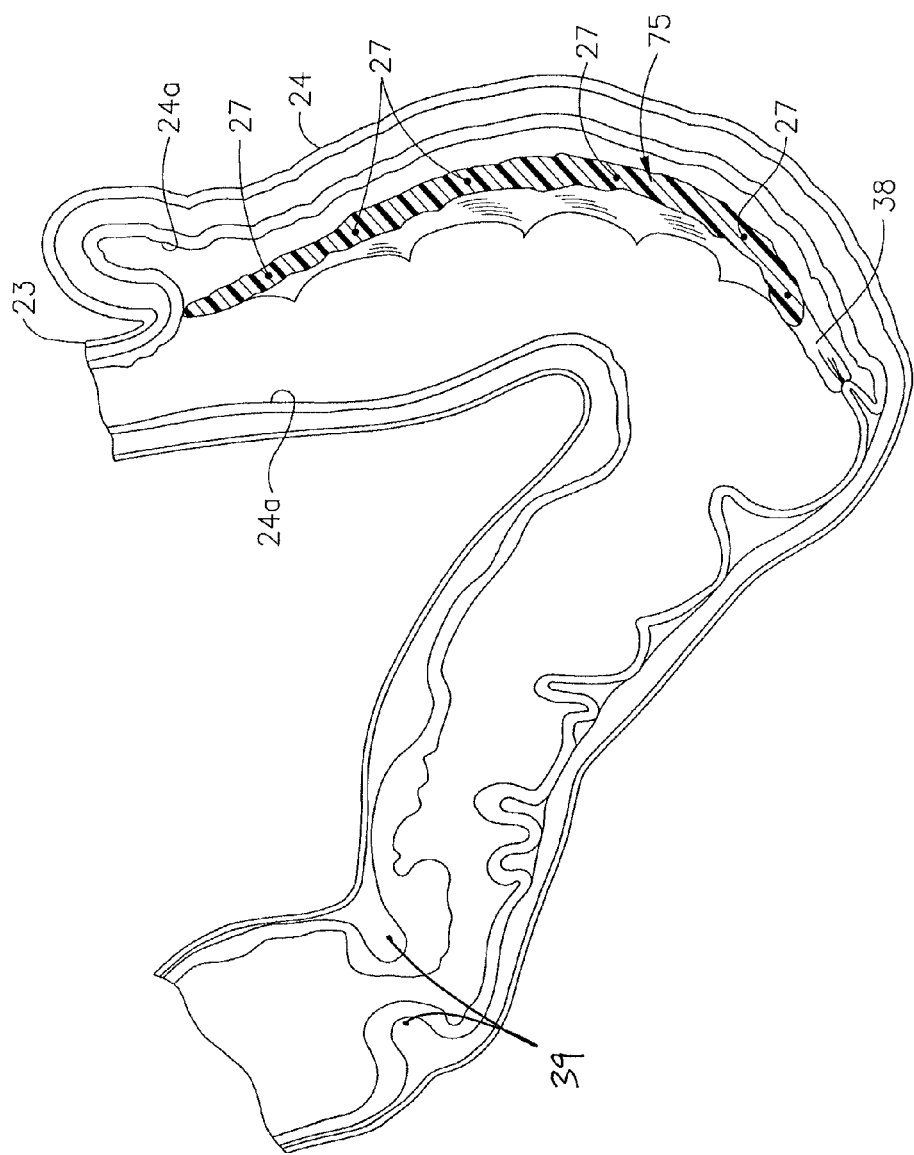
FIG. 6 is a front cross-sectional view of the stomach illustrating the completed implant partition structure and a route whereby food travels from the esophagus through the stomach.

As also seen in FIG. 6, a passageway 38 is provided between the two partitioned volumes for food to pass should any food accidentally enter the blocked volume. Arrow 31 represents the mode by which food will exit the stomach 24. The food will exit via passageway 38. Passageway 38 will be constructed generally adjacent to where the stomach 24 connects to the pyloric sphincter 39. This passageway 38 will permit food that accidentally enters the blocked volume to exit the stomach 24.

Finally, FIG. 6 represents a front, cross-sectional view of the stomach 24 having the wall 29 partitioning the stomach 24 into two separate volumes. Food travels into the stomach 24 and passes through the stomach 24 in the area surrounded by the stomach 24 adjacent to the pyloric sphincter 39 and the wall 29. Food exits the stomach by way of the pyloric sphincter 39. Any food that accidentally travels into the blocked volume is still able to leave the stomach 24 via passageway 38.

It will be recognized that equivalent structures may be substituted for the structures illustrated and described herein and that the described embodiment of the invention is not the only structure which may be employed to implement the claimed invention. As one example of an equivalent structure which may be used to implement the present invention, differing endoscopes may be used depending upon their structure, design, and complexity. As a further example of an equivalent structure which may be used to implement the present invention, a pressure source besides a plunger may be used to advance the expandable foam through the endoscope into the stomach. In addition, it should be understood that every structure described above has a function and such structure can be referred to as a means for performing that function.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A method for partitioning the stomach with at least one or more filaments and an expandable adhesive foam, wherein the at least one or more filaments are configured to be attached to the walls of the stomach, the method comprising:
    (a) forming a web structure within the stomach with the at least one or more filaments, wherein the web structure is formed by attaching the at least one or more filaments to the walls of the stomach such that the location of adjacent attachment points between the at least one or more filaments and the walls of the stomach are such that the attachment points alternate being located on opposing positions within the stomach;
    (b) applying the expandable adhesive foam to the web structure, wherein the expandable adhesive foam is foamed into place about the web structure and the stomach, wherein the expandable adhesive foam is formed from:
        (i) an adhesive compound;
        (ii) a foaming agent; and
        (iii) an adhesive initiator; and
    (c) allowing the expandable adhesive foam to set to form a substantially continuous and substantially flat foam wall in the interior of the stomach to partition the stomach into at least two portions.

2. A method for partitioning the stomach with at least one or more filaments and an expandable adhesive foam, the method comprising:
    a) constructing a web structure with the at least one or more filaments, wherein the web structure comprises a zig zag pattern of filament to form the web structure, wherein the web structure is constructed within the stomach to be partitioned such that as the web structure is constructed, the web structure is attached to the interior wall of the stomach such that the web structure is tensioned such that when attached to the stomach wall, the web structure does not cause the stomach wall to inwardly collapse;
    b) applying the expandable adhesive foam to the web structure; and
    c) allowing the expandable adhesive foam to set to form a substantially continuous and substantially flat foam wall in the interior of the stomach to partition the stomach into a food digestion portion and at least one empty portion, wherein the foam wall further comprises one or more passageways between the food digestion portion and the at least one empty portion of the stomach, the one or more passageways being located near an exit portion of the stomach and enabling food and liquids to exit from the at least one empty portion.

3. The method of claim 2 wherein the web structure includes at least one penetration device to penetrate and attach the web structure to the stomach wall.

4. The method of claim 3 wherein the at least one penetration device comprises a needle.

5. The method of claim 2 wherein the web structure is absorbable and is constructed from a material selected from a group consisting of:
    a) catgut;
    b) polyglycolic acid;
    c) polyglactin;
    d) polydioxanone; and
    e) polyglyconate.

6. The method of claim 2 wherein the web structure is non-absorbable and is constructed from a material selected from a group consisting of:
    a) silk;
    b) nylon;
    c) dacron;
    d) polypropylene;
    e) braided polyester; and
    f) polybutester.

7. The method of claim 2 wherein the expandable adhesive foam is foamed into place about the web structure and the stomach, wherein the expandable adhesive foam is formed from:
    a) an adhesive compound;
    b) a foaming agent; and
    c) an adhesive initiator.

8. The method of claim 7 wherein the adhesive compound is selected from a group consisting of polymerizable monomer, a polymerizable 1,1, 1,1-disubstituted ethylene monomer, a cyanoacrylate formulation, monomers and monomer systems, acrylate, epoxy, urethane, silicone, silicone rubber, photopolymerizable compositions, vinyl-terminated monomers, gelatin resorcinol formaldehyde, gelatin resorcinol glutaraldehyde, anhydrides cross-linked with polyols, hyaluronic acid cross-linked with hydrazines, mixed monomer systems and co-polymers.

9. The method of claim 8 wherein the foaming agent is selected from a group consisting of pentane, hexane, heptane, 1,1,2-trichlorotrifluoro-ethane, 1,1,1-trichlorotrifluoroethane-, petroleum ether, diethyl ether, cyclopentane, cyclohexane, benzene, carbon tetrachloride, chloroform, methylcyclopentane, dimethylsulfide, 1,1-dichloroethane, 1,1,1-trichloroethane, perfluorohexane, perfluoroheptane, and 1-bromopropane.

10. The method of claim 9 wherein the adhesive initiator polymerizes the adhesive compound and the adhesive initiator is selected from a group consisting of moisture, detergent compositions, surfactants, phosphines, phosphites, phosphonium salts, alcohols inorganic bases, inorganic salts, sulfur compounds, cyclic carbonates, acyclic carbonates, organometallics, radical initiators, and radicals.

11. The method of claim 7 wherein the act of applying the expandable adhesive foam is performed with an adhesive foam system, wherein the adhesive foam system comprises:
    a) a pump;
    b) a housing containing the adhesive, the foaming agent, and the adhesive initiator and operably coupling the adhesive, the foaming agent, and the adhesive initiator to the pump;
    c) a cannula having at least one passageway extending therethrough, the at least one passageway operably connected to one or more of the adhesive, the foaming agent, and the adhesive initiator and the pump for passage of one or more of the adhesive, the foaming agent, and the adhesive initiator therethrough; and d) a mixer located downstream from the pump to mix two or more of the adhesive, the foaming agent, and the adhesive initiator together.

12. The method of claim 11 wherein the cannula is flexible.

13. The method of claim 12 further including a nozzle attached to the cannula for dispensing the expandable adhesive foam therefrom, the nozzle having at least one foam dispersement opening therein.

14. The method of claim 11 wherein the adhesive is at least one selected from a group consisting of polymerizable monomer, a polymerizable 1,1,1-disubstituted ethylene monomer, a cyanoacrylate formulation, monomers and monomer systems, acrylate, epoxy, urethane, silicone, silicone rubber, photopolymerizable compositions, vinyl-terminated monomers, gelatin resorcinol formaldehyde, gelatin resorcinol glutaraldehyde, anhydrides cross-linked with polyols, hyaluronic acid cross-linked with hydrazines, mixed monomer systems and co-polymers.

15. The method of claim 11 wherein the foaming agent is selected from a group consisting of pentane, hexane, heptane, 1,1,2-trichlorotrifluoro-ethane, 1,1,1- trichlorotrifluoroethane-, petroleum ether, diethyl ether, cyclopentane, cyclohexane, benzene, carbon tetrachloride, chloroform, methylcyclopentane, dimethylsulfide, 1,1-dichloroethane, 1,1,1-trichloroethane, perfluorohexane, perfluoroheptane, and 1-bromopropane.

16. The method of claim 15 wherein the foaming agent is a pressurized gas, the pressurized gas pumping the adhesive foam from the nozzle.

17. The method of claim 11 wherein the adhesive initiator polymerizes the adhesive compound of the adhesive foam, and the adhesive initiator is selected from a group consisting of moisture, detergent compositions, surfactants, phosphines, phosphites, phosphonium salts, alcohols inorganic bases and salts, sulfur compounds; cyclic carbonates, acyclic carbonates, organometallics, radical initiators, and radicals.

* * * * *